US005091308A

United States Patent [19]
Klegerman et al.
[11] Patent Number: 5,091,308
[45] Date of Patent: Feb. 25, 1992

[54] PROCESS FOR THE ENZYMATIC DISPERSAL OF *MYCOBACTERIUM BOVIS* - BCG

[75] Inventors: Melvin E. Klegerman, Chicago; Michael J. Groves, Lake Forest, both of Ill.

[73] Assignee: The Board of Trustees of the University of Illinois, Chicago, Ill.

[21] Appl. No.: 471,505

[22] Filed: Jan. 29, 1990

[51] Int. Cl.[5] ........................... C12P 9/50; C12N 1/20

[52] U.S. Cl. ................................ 435/68.1; 435/253.1; 424/92; 424/93 D

[58] Field of Search ............... 435/252.4, 252.5, 253.1, 435/68.1; 424/92, 93

[56] References Cited

U.S. PATENT DOCUMENTS

| | | | |
|---|---|---|---|
| Re. 33,164 | 2/1990 | Brown et al. | 424/89 |
| 4,657,761 | 4/1987 | Pinto | 424/92 |
| 4,748,112 | 5/1988 | Fareed et al. | 424/88 |
| 4,777,130 | 10/1988 | Maes | 424/87 |

OTHER PUBLICATIONS

Abaas, Acta Pathol. Microbiol. Immunol. Scand. Seet B Microbiol, vol. 93(1), pp. 15–20 (1985).

Abaas et al., Acta Pathol. Microbiol. Immunol. Scand. Seet B Microbiol., vol. 91 (5) pp. 317–24 (1983).

Abaas et al., Scand. J. Dent. Res. 90(2) 109–116 (1982).

Abaas et al., Scand. J. Dent. Res. 89(5) pp. 366–373 (1981).

Hardham et al., Microbios. Letters, vol. 13, pp. 33–42.

*Primary Examiner*—F. T. Moezie

*Assistant Examiner*—Andrew G. Rozycki

*Attorney, Agent, or Firm*—Allegretti & Witcoff, Ltd.

[57] ABSTRACT

*Mycobacterium bovis* BCG suspensions are treated with a protease enzyme such as pronase, resulting in the production of suspensions having smaller aggregates and single cells. Such suspensions, when processed into vaccines, exhibit improved immunizing potential against cancer and would be expected to exhibit improved immunizing potential against tuberculosis.

9 Claims, 5 Drawing Sheets

TICE BCG
LOT 105178
FREEZE-DRIED WASHED
UNTREATED CELL AGGREGATES

TICE BCG
LOT 105178
FREEZE-DRIED WASHED
UNTREATED SINGLE CELLS AND
SMALL AGGREGATES

TICE BCG
LOT 105178
AFTER 24 HOURS PRONASE
 DISPERSED CELLS

TICE BCG
LOT 105178
AFTER 24 HOURS PRONASE
  DISPERSED CELLS

TICE BCG
LOT 105178
AFTER 48 HOURS PRONASE SPHERULES
OF SEPARATED COVERING MATERIAL

PROCESS FOR THE ENZYMATIC DISPERSAL OF *MYCOBACTERIUM BOVIS* - BCG

BACKGROUND OF THE INVENTION

Vaccines containing various living avirulent cells of tubercle bacilli, in particular Bacillus Calmette-Guerin (BCG), an attenuated bovine tuberculosis organism (*Mycobacterium bovis*), have been used to induce immunity against acquired tuberculosis disease in man. Recently, BCG vaccine has been used as an immunostimulant in the treatment of cancer. See Rosenthal, 1980, BCG Vaccine: Tuberculosis-Cancer, P.S.G. Publishing, Littleton, Mass. and Lamoureux et al., 1976, BCG in Cancer Immunotherapy, Grune & Stratton, New York.

In the preparation of these vaccines, *M. bovis* BCG is grown in a suitable nutrient medium and then harvested. However, during the growth phase, the cells of *M. bovis* BCG tend to aggregate, making the production of a homogenous vaccine very difficult. Please see Hardham and James, Microbios Letters 13: 33-42 (1980).

This paper suggests suppressing the aggregation by the inclusion of a wetting agent in the growth medium, but the suppression of aggregation, which is marginal, ceases as soon as the wetting agent is removed. It was disclosed that there is a covering material, possibly a polysaccharide, which appears to hold the cells together in aggregates. Other investigators also observed the aggregation of BCG cells. See for example Davis et al., 1968, Microbiology, Harper & Row, Evanston, IL, p.845.

The tendency of BCG cells to aggregate during the growth phase makes the standardization, evaluation and formulation of the vaccine problematic. For example, vaccine efficacy for both tuberculosis prophylaxis and cancer immunotherapy has been attributed to the presence of living cells in the vaccine, and adverse effects, including enhancement of tumor growth, have been related to the quantity of dead cells. Please see Youmans and Youmans, 1971, Immunization in Tuberculosis, DHEW Publ. No. (NIH) 72-68, pp. 219-236; Hersch et al., JAMA 235: 646-650 (1976), and Werner et al., Bull. Inst. Pasteur 75: 5-84 (1977). For these reasons, dispersal of BCG aggregates into smaller particles or single cells would therefore enable better evaluation of the vaccine at various stages of production and, most important, would increase the number of therapeutic doses per lot by increasing the number of colony-forming units (CFU) per unit volume of vaccine.

BRIEF DESCRIPTION OF THE DRAWINGS

The attached FIGS. (1-5) are scanning electron micrographs (SEM) of untreated and pronase-treated BCG. The figures illustrate the cell dispersion effected by enzyme treatment.

SUMMARY OF THE INVENTION

Figure 1:
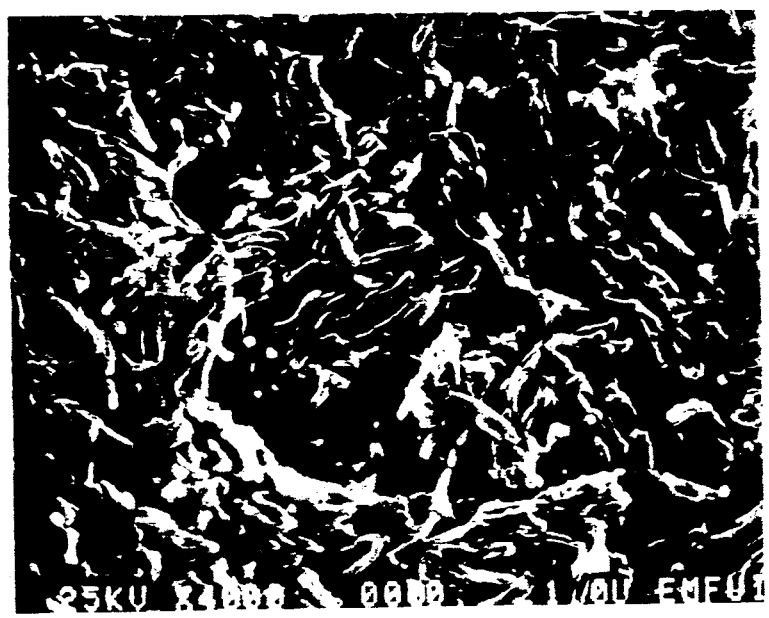
FIG. 1 is an SEM of untreated, washed Tice ™ BCG reconstituted from freeze-dried vaccine. This figure shows a preponderance of large aggregates that contain more than 90% of cells in the suspension. Additionally, this figure reveals that the aggregated BCG is covered by an amorphous substance.
Figure 2:
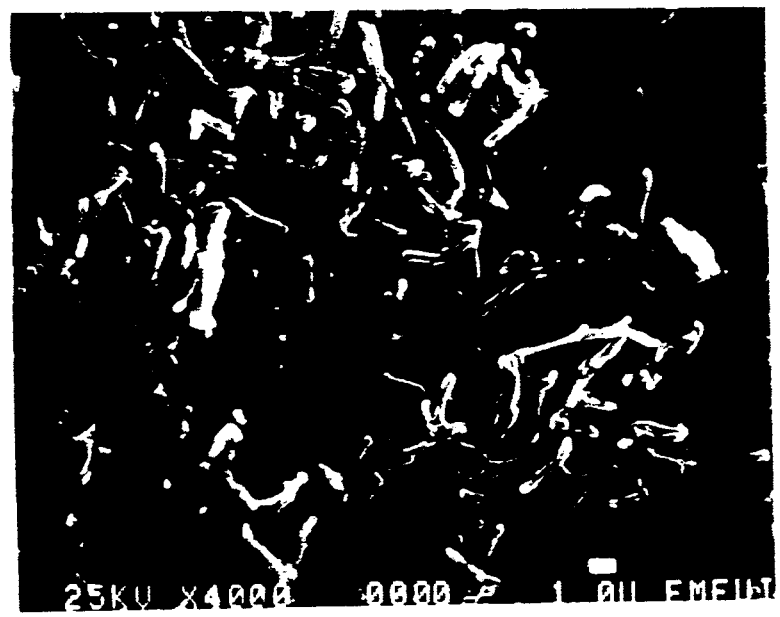
FIG. 2 is an SEM of single cells and small aggregates from the untreated, washed BCG suspension. This figure also demonstrates that the covering material is not found on single cells.
Figure 3:
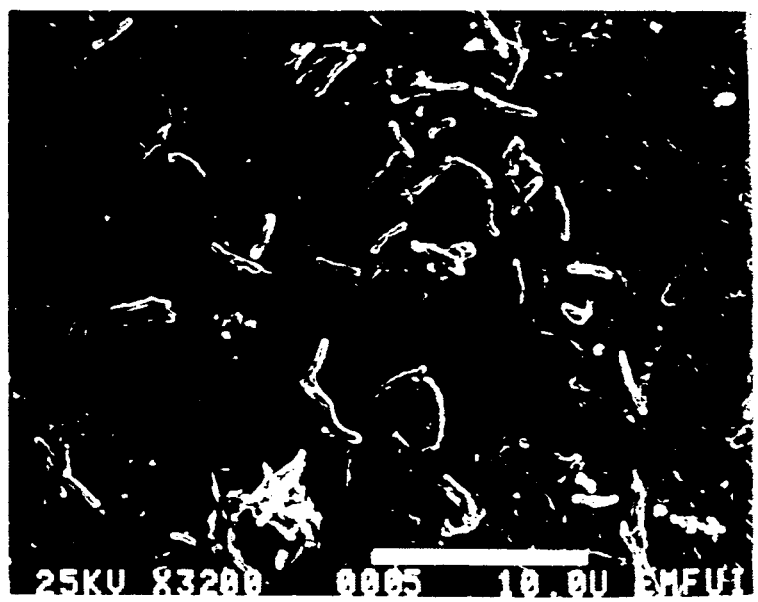
FIG. 3 is an SEM of dispersed cells after pronase treatment for 24 hours.
Figure 4:
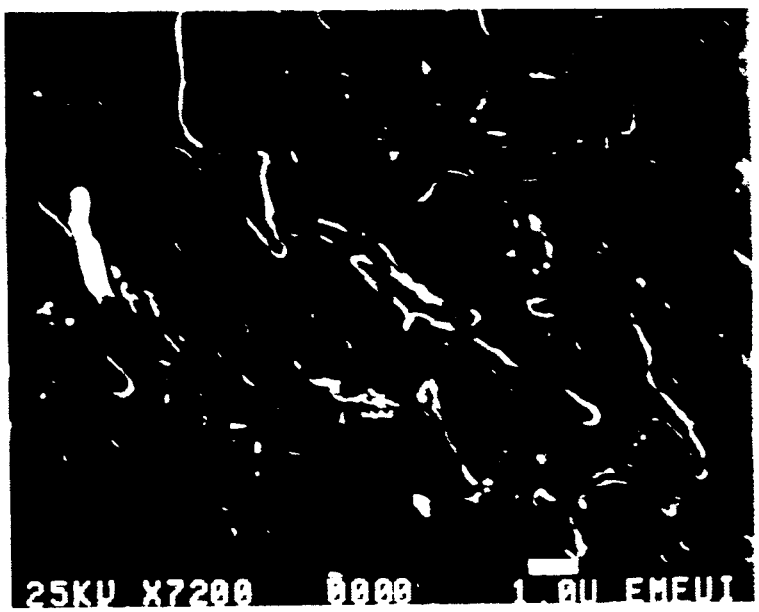
FIG. 4 is an SEM of dispersed cells after pronase treatment for 24 hours. This figure shows single cells coated with residual covering material, an occurrence not observed in untreated BCG, demonstrating dispersal of previously aggregated cells.
Figure 5:
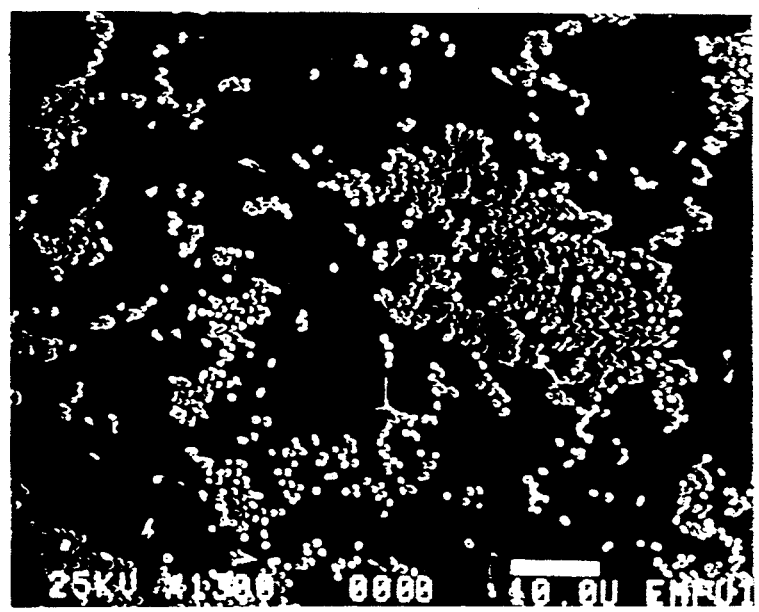
FIG. 5 is an SEM of spherules of separated covering material after 48-hours pronase treatment. The spherules of separated covering material are not seen in untreated BCG.

Cells of *M. bovis* BCG are grown as a surface pellicle on a suitable liquid medium or they are grown in a fermenter containing an aqueous medium. They are harvested. A sterile enzyme solution containing an effective amount of the enzyme to degrade the covering material is added to the BCG pellicle in a buffer solution or a BCG suspension resulting from the fermenter culture. The suspension is stirred until dispersal is complete. The resultant suspension is concentrated and washed free of enzyme and is thereafter resuspended to optimal therapeutic concentration with a cryoprotectant solution, after which it is distributed into ampoules and lyophilized. In use, the clinician reconstitutes the lyophilized cells with a suitable vehicle such as "Water for Injection" before administration to patients.

DETAILED DESCRIPTION

The present invention relates to a process for the dispersal of a living culture of *M. bovis* into smaller aggregates, preferably into individual or single cells. The resulting suspension is processed into BCG vaccine which exhibits more enhanced immunological properties than the untreated suspension. The present invention also includes within its scope the BCG vaccine comprising the treated *M. bovis*.

In a typical practice of the present invention, cells of *Mycobacterium bovis*-BCG are grown and harvested by methods known in the art. For example, they may be grown as a surface pellicle on a Sauton medium or in a fermentation vessel containing the dispersed culture in a Dubos medium. Please see Dubos et al., Am. Rev. Tuber. 56: 334–45 (1947) and Rosenthal, Am. Rev. Tuber. 35: 678–84 (1937). All the cultures are harvested after 14 days incubation at about 37° C. Cells grown as a pellicle are harvested by using a platinum loop whereas those from the fermenter are harvested by centrifugation or tangential-flow filtration. The harvested cells are re-suspended in an aqueous sterile buffer medium. A typical suspension contains from about $2 \times 10^{10}$ cells/ml to about $2 \times 10^{12}$ cells/ml. To this bacterial suspension, a sterile solution containing a selected enzyme which will degrade the BCG cell covering material is added. The resultant suspension is agitated such as by stirring to ensure maximal dispersal of the BCG organisms. Thereafter, a more concentrated cell suspension is prepared and the enzyme in the concentrate removed, typically by washing with an aqueous buffer, employing known techniques such as tangential-flow filtration. The enzyme-free cells are adjusted to an optimal immunological concentration with a cryoprotectant solution, after which they are filled into vials, ampoules, etc., and lyophilized, yielding BCG vaccine, which upon reconstitution with water is ready for immunization.

We have found the nonspecific protease enzyme, pronase, obtained from *Streptomyces griseus*, particularly suitable for our process although other enzymes that will degrade the covering material or structures linking it to cells will be equally suitable.

An amount of enzyme sufficient to degrade the cell covering material is employed. In the pronase treatment, for example, 0.5 mg of enzyme per mg dry weight of the BCG cells is employed. To ensure complete dispersion of the enzymes, the resulting suspension is typically stirred at 37° C. for 24 hours. An additional equal amount of the enzyme solution is then added and the stirring continued for another 24 hours. The separated cell covering material often occurs as spherules which are readily separated by known methods such as by buoyant density centrifugation or by adsorbing of BCG cells to an anionic support, followed by elution with an alkali. The foregoing process is suitable for dispersing substrains of *M. bovis* BCG such as the Tice or Glaxo substrains.

EXAMPLE 1

This example illustrates the fact that BCG colonies can be dispersed and broken down into individual cells or smaller aggregates as a result of being treated with pronase and following a subsequent 48-hour incubation period.

A buffer solution having the following formula was prepared: 0.05M $PO_4$ buffer which comprised 0.71 g of $Na_2HPO_4$ and 90 ml of $H_2O$. The pH of the solution was adjusted to 8.0 with 1N HCl and the volume was brought to 100 ml with q.s. water. One ampoule of BCG Tice strain #105178 (dry cell weight=15.6 mg) was reconstituted with 1 ml $H_2O$. 9 ml of $PO_4$ buffer solution was added to the bacteria in a 17×100 mm snap top plastic tube. 1 ml of the resulting suspension was then removed and transferred to a 13×100 mm glass screw top tube to be used as the 0 hr control. This was heated in a boiling bath for 15 minutes. 0.1 ml was then added to 200 ml of Hematall R and a Coulter size distribution analysis was performed according to the technique set forth in Pharmaceutical Research, Vol. 5, No. 9, 1988, pp. 608-10.

The remaining 9 ml of BCG in the plastic test tube was then treated with 10 mg of pronase in 1 ml of $PO_4$ buffer. The pronase was obtained from *Streptomyces griseus* (Protease Type XIV, Sigma Chem. Co., St. Louis, MO). This suspension was then vortexed and incubated at 37° C. At various time intervals, eg., 1, 2, 24, and 48 hours, 1 ml of the sample was removed and Coulter cell-size distribution analysis was performed as above.

The effect of pronase on BCG dispersal at various time intervals, including 0 hr and 48 hrs, was then observed using the results above (See FIGS. 3, 4, and 5) and compared to the results found with non-treated BCG (See FIGS. 1 and 2).

We claim:

1. A process for the production of a suspension of *Mycobacterium bovis*-BCG having aggregates or single cells which comprises:

a) adding a sterile pronase enzyme solution containing an effective amount of said enzyme which will degrade the covering material of a BCG cell to a BCG pellicle in a buffer solution or BCG in an aqueous suspension, b) agitating the resulting mixture until the enzyme solution is completely dispersed, c) concentrating the resultant suspension, and d) removing the enzyme from the suspension yielding said desired *Mycobacterium bovis*-BCG.

2. A process according to claim 1 in which said pronase is derived from *Streptomyces griseus.*

3. A process according to claim 1 wherein 0.5 mg of pronase per mg dry weight of BCG is added.

4. A process according to step "b" of claim 1 wherein the mixture is agitated at 37° C. for 24 hours.

5. A process according to claim 1 wherein the mixture containing the pronase is first agitated at 37° C. for 24 hours, then an equal amount of pronase is added and the agitation is continued for an additional 24 hours at 37° C.

6. A process according to claim 1 wherein said *Mycobacterium bovis*-BCG is the Tice-substrain.

7. A process according to claim 1 wherein said *Mycobacterium bovis*-BCG is the Glaxo substrain.

8. A process according to step "b" of claim 1 wherein agitation to effect dispersal is accomplished by stirring.

9. A process according to claim 1 wherein said suspension contains from about $2\times10^{10}$ cells/ml to about $2\times10^{12}$ cells/ml.

* * * * *